United States Patent [19]

Kaplan

[11] 4,246,904

[45] Jan. 27, 1981

[54] SURGICAL SUTURE DERIVED FROM SEGMENTED POLYETHER-ESTER BLOCK COPOLYMERS

[75] Inventor: Donald S. Kaplan, Ridgefield, Conn.

[73] Assignee: American Cyanamid Company, Stamford, Conn.

[21] Appl. No.: 7,076

[22] Filed: Jan. 29, 1979

Related U.S. Application Data

[63] Continuation-in-part of Ser. No. 933,224, Aug. 14, 1978.

[51] Int. Cl.³ .............................................. A61L 17/00
[52] U.S. Cl. .............................. 128/335.5; 206/63.3; 525/444
[58] Field of Search ............... 128/335.5; 206/63.3; 260/860

[56] References Cited

U.S. PATENT DOCUMENTS

| | | | |
|---|---|---|---|
| 3,359,983 | 12/1967 | Northey | 128/335.5 |
| 3,652,713 | 3/1972 | Okazaki | 260/860 |
| 3,766,146 | 10/1973 | Witsiepe | 260/860 |
| 3,784,520 | 1/1974 | Hoeschele | 260/860 |
| 3,861,521 | 1/1975 | Burtz | 128/335.5 |
| 3,875,946 | 4/1975 | Duncan | 128/335.5 |
| 4,032,993 | 7/1977 | Coquard et al. | 128/335.5 |
| 4,127,127 | 11/1978 | Wong et al. | 128/260 |

FOREIGN PATENT DOCUMENTS 2265294 4/1977 Fed. Rep. of Germany .

OTHER PUBLICATIONS

J. Polymer Science, vol. XIV, pp. 15-28, (1954).
J. Polymer Science, Symp. #48, pp. 47-60, (1974), Buck et al.

Primary Examiner—Robert W. Michell
Assistant Examiner—C. F. Rosenbaum
Attorney, Agent, or Firm—Charles F. Costello, Jr.

[57] ABSTRACT

A synthetic nonabsorbable surgical suture compound of segmented polyether—ester block copolymers is disclosed.

8 Claims, No Drawings

4,246,904

SURGICAL SUTURE DERIVED FROM SEGMENTED POLYETHER-ESTER BLOCK COPOLYMERS

CROSS REFERENCE TO OTHER APPLICATIONS

This application is a Continuation-In-Part of U.S. application Ser. No. 933,224 filed Aug. 14, 1978.

BACKGROUND OF THE INVENTION

This invention relates to a surgical suture composed of block polyether-esters which contain (1) a polymeric block of polyalkene esters and (2) a polymeric block of aromatic dicarboxylic acids or cycloaliphatic acids with short chain aliphatic or cycloaliphatic diols. This surgical suture can be a monofilament, or a twisted or braided multifilament article.

The medical profession is continuously seeking more satisfactory sutures to be used in closing wounds, whether such wounds are incisions from operations, or tears, cuts or abrasions from accidental or other causes. Many materials have been suggested for use as sutures. Sutures are divided into two broad classes, the absorbable sutures, such as catgut or polyglycolic acid sutures, which are absorbed by the body tissues, and nonabsorbable sutures which either remain in the tissues in substantially their original form for prolonged periods or are removed from the skin surfaces after the underlying tissues have been healed. For non-absorbable sutures many materials have been suggested which range from cotton and silk through various synthetic filaments such as polypropylene to stainless steel or nickel or other metallic filaments.

Other things being equal, the medical profession usually prefers the suture which is strongest. In spite of many disadvantages stainless steel has met with considerable acceptance because of its extremely high tensile strength. Such plastic materials as polypropylene are meeting currently with considerable commercial acceptance because of comparatively high tensile strength and because of other advantages over stainless steel.

Additionally, the suture material needs good handling characteristics. The handling characteristics of a suture, as a general statement, are difficult to define but should include a high degree of flexibility.

Handling characteristics include knot strength and knot security. That is, the suture must have such characteristics that a knot can be tied in the suture. Some materials are so brittle that if a suture made from them is knotted, the strength of the suture is markedly reduced. For some materials an overhand knot in a strand can reduce the strength of the strand by a factor of two or more. In addition to knot strength, the suture should have such characteristics that the knot when tied remains in position. Also, the suture should be "throwable" so that when the free end is placed in position by the surgeon it will remain in that position until moved. Similarly, the suture should have such characteristics that it can be thrown or moved from side to side and yet retain the position into which it is thrown.

A surgical suture comprising a high degree of tensile strength with a high degree of flexibility is therefore needed in the medical profession.

A polypropylene monofilament suture is one attempt at solving this need. The tensile strength of this suture is good when compared to stainless steel; and the flexibility of the suture, though better than stainless steel, is still considered to be stiff and springy. See, e.g., U.S. Pat. No. 3,630,205 which is incorporated herein by reference.

A polyurethane suture is another attempt. The primary advantage of this suture is its very high degree of flexibility. However, this has low tensile strength and extremely high elongations at break which make it unsatisfactory for general wound closure methods. See, e.g., U.S. Pat. No. 3,454,011 which is incorporated herein by reference.

Other attempts include the braiding of materials with a high tensile strength but a low degree of flexibility. Dacron ® is an example of a suture with a satisfactory tensile strength after braiding and an increased degree of flexibility. A monofilament suture is generally preferred in most surgical procedures to a braided suture because of the reduced tissue drag of the monofilament. Also, in skin suturing a monofilament suture is generally preferred because it is usually less susceptible to capillary action than a braided suture.

This invention has advantages over these prior art attempts. The suture of this invention shows excellent strength and flexibility as a monofilament. Specifically, the surgical suture of this invention combines the tensile strength of a suture such as a polypropylene monofilament suture, with the flexibility of a braided or polyurethane suture.

SUMMARY OF THE INVENTION

The discovery has now been made that a non-absorbable monofilament sterile surgical suture or ligature is comprised of a polymeric block (A) consisting of a polyalkylene ether of the formula

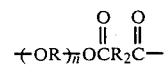

having a number average molecular weight of from about 500-3000 wherein R is a straight or branched chain alkyl group of from about 2 to 10 carbon atoms and $R_2$ is 1,4-phenylene or cyclohexylene and n is the number of repeating units; and a polymeric block (B) which is the reaction product of an aromatic dicarboxylic acid or a cycloaliphatic acid, and a short chain aliphatic or cycloaliphatic diol, having the formula

wherein $R_1$ is a straight or branched chain alkyl group of from about 2 to 10 carbon atoms or a cyclic group having the formula

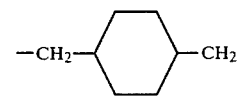

; and $R_2$ is 1,4-phenylene or cyclohexylene; and the block (B) comprising from about 30% to 95% of the copolymer. The copolymer has a number average molecular weight of from about 25,000 to 30,000. This suture has good flexibility, good fatigue life and high tensile strength.

The surgical suture or ligature wherein the polymeric block (B) comprises from about 55% to 80% of the copolymer is most preferred.

The surgical suture or ligature described above wherein R is selected from the group consisting of ethylene, propylene or butylene is also preferred, and where R is butylene is most preferred.

Within the scope of this invention is the surgical suture or ligature described above having an attached needle.

The non-absorbable monofilament sterile surgical suture or ligature described above has approximately the following characteristics:

| | |
|---|---|
| Straight Pull, pounds per square inch | At least about 50,000 |
| Knot Pull, pounds per square inch | At least about 35,000 |
| Flexual Modulus, pounds per square inch | Less than about $3.5 \times 10^5$ |
| Flexual Fatigue, cycles to failure | At least about 1,000 |
| Elongation at break, percent | Less than about 100% |
| Draw ratio | Between about $5\times$ and $10\times$ |

The surgical suture wherein the Elongation at break percent is between about 25 and 55 is preferred.

Within the scope of this invention is a surgical suture package comprising a sterile enclosure and therein a non-absorbable monofilament sterile surgical suture or ligature described above comprising a polymeric block (A) consisting of a polyalkylene ether of the formula

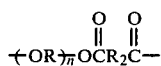

having a number average molecular weight of from about 500–3000 wherein R is a straight or branched chain alkyl group of from about 2 to 10 carbon atoms and $R_2$ is 1,4-phenylene or cyclohexylene; and a polymeric block (B) which is the reaction product of an aromatic dicarboxylic acid or a cycloaliphatic acid, and a short chain aliphatic or cycloaliphatic diol, having the formula

wherein $R_1$ is a straight or branched chain alkyl group of from about 2 to 10 carbon atoms or a cyclic group having the formula

and $R_2$ is 1,4-phenylene or cyclohexylene, and the block (B) comprising from about 30% to 95% of the copolymer. The copolymer has a number average molecular weight of from about 25,000 to 30,000. The suture or ligature has good flexibility, good fatigue life and a high tensile strength. The surgical suture package wherein R in the copolymer is butylene is preferred.

DESCRIPTION OF THE INVENTION

These sutures combine the advantages of a braided suture material (i.e., flexibility and knot security) and those of a monofilament suture material (i.e., smooth surface, low tissue drag, inertness, and ease of knot run down). Specifically, these sutures are non-absorbable monofilament sutures which combine flexibility fatigue life, and high tensile strength.

The structures of the block copolymers of this invention may be represented by the following general formula:

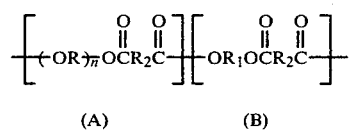

wherein R and $R_1$ are the same or different straight or branched chain alkyl groups of 2 to 10 carbon atoms; $R_2$ is selected from the group comprising phenylene and cyclohexylene; and n is the number of repeating units.

In the polymeric block A, for example, polyethylene oxide or polybutylene oxide may constitute the soft segment of the block copolymer.

In the polymeric block B, for example, polyethylene terephthalate or polybutylene terephthalate may constitute the hard segment of the block copolymer.

In order to have the desired qualities of flexibility and high tensile strength, the sutures of this invention must be formed from a copolymeric mixture of blocks A and B, wherein the hard segment B constitutes 30–95% of the mixture. Preferably, the B component should constitute 50–85% of the mixture.

Generally, the soft segment A is derived from a (tetramethylene ether)glycol having a number average molecular weight in the range of about 500–3000 may be used. The total number average molecular weight of the block polyether-esters is about 25–30,000.

The hard segment B can be derived from (1) a diacid, for example, (a) terephthalic acid, or,

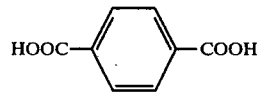

(b) 1,4-cyclohexane dicarboxylic acid, or

(c) from the dimethyl esters of these acids; and, (2) a short chain glycol, for example, (a) a linear or branched chain glycol of 2 to 10 carbon atoms; and preferably of 4 carbon atoms, or, (b) 1,4-cyclohexanedimethanol, or,

(c) 1,4-bis(hydroxymethyl)benzene The reaction product of (1) and (2) forms the hard segment B.

The methods for preparing these block copolymers are known in the art. See, e.g., Great Britain Pat. No.

1,458,341 published Dec. 15, 1976; U.S. Pat. No. 3,763,109 issued Oct. 2, 1973; and U.S. Pat. No. 3,766,146 issued Oct. 16, 1973 which are incorporated herein by reference.

Sutures formed from the block copolymers described in this application, when extruded and drawn from 5X to 10X (where X is the original length of the undrawn strand), preferably from 6X to 8X, have the desired qualities of flexibility, fatigue life, tensile strength, knot security, smooth surface, low tissue drag, inertness and ease of knot run down.

The sutures formed from the block copolymers in accordance with this invention can be sterilized by a variety of methods recognized in the art including exposure to a gaseous sterilizing agent such as ethylene oxide, and exposure to radiation of gamma rays. Generally, the sutures of this invention cannot be sterilized by exposure to heat because the flexible properties of the sutures may be effected.

The sutures of this invention can be colored by mechanically blending with a pigment. Pigments such as titanium dioxide, iron oxide or carbon black give identifiable colors. Other colored pigments which do not cause deleterious tissue reactions may also be used to impart color to the strands. Other colored pigments which may also be used are disclosed in U.S. Pat. Nos. 3,636,956; 3,297,033 and 2,909,177 and British Patent 1,375,008. These patents are incorporated herein by reference.

The sutures formed from the block copolymers of this invention were tested for toxicity by placing two 4 cm. segments on each of three plates of HEp-2 cell culture. The cultures were incubated for 24 hours at 36° C., stained with crystal violet and checked for degeneration of the cell monolayer in the area of the suture segment. None of the suture segments showed any evidence of cytotoxicity.

The sutures were also tested in mice by the Systemic Injection Test according to the U.S.P. Biological Test for Plastic Containers No. 19. The sutures were subjected to an extraction procedure and the extractant was injected into mice. No adverse reactions were observed in any of the test animals.

For use as sutures, any size may be used, depending upon the preference of the surgeon. In the United States the more common standard sizes are the United States Pharmacopeia, which is abbreviated U.S.P., sizes (United States Pharmacopeia Convention, Inc., Mack Publishing Co., Easton, Pa.).

| U.S.P. Size | U.S.P. Diameter (inches max.) |
|---|---|
| 6-0 | 0.004 |
| 5-0 | 0.006 |
| 4-0 | 0.008 |
| 3-0 | 0.010 |
| 00 | 0.013 |
| 0 | 0.016 |

The results of tests conducted to compare three types of non-absorbable sutures: (1) Dermalon ®, a nylon suture American Cyanamid Company, Wayne, New Jersey; and (2) Surgilene ®, a polypropylene suture of American Cyanamid Company, Wayne, New Jersey; and (3) the copolymers of this invention are disclosed in the following examples.

EXAMPLE 1

A copolyester composed of a polytetramethylene oxide soft segment (MW=1000) and a poly(tetramethylene terephthalate) hard segment and containing 58±2% of the hard segment is extruded at 230°–245° C. with a collection of extrudate at about 25 feet per minute. A two stage draw was used with an 8X draw at 160° C. in zone 1 and 1.1X draw at 120° C. in zone 2 for a total draw of 8.8X. The properties of this size 3/0 USP fiber (0.245 mm) are described in the Table I below.

EXAMPLE 2

A copolyester composed of the hard and soft segments of Example 1 but at a ratio of 76% hard segment is extruded at 230°–245° C. A two stage draw is used where zone 1 is at 165° C. and drawn 2X and zone 2 is drawn 3.5X at 150° C. for a total draw of 7.0X. The properties of this size 3/0 U.S.P. fiber (0.231 mm) are described in the Table I below.

EXAMPLE 3

A copolyester composed of the hard and soft segments of Example 1, but at a ratio of 66% hard segment is extruded at 230°–245° C. A two stage draw is used where Zone 1 is at 320° F. and drawn 2X and Zone 2 is at 320° F. and drawn at 4.1 for a total draw of 8.2X. The fiber is then heated at constant length at 185° C. for 10 minutes. The properties of this fiber (0.195 mm diameter) are described in Table 1.

TABLE I

| | STRAIGHT[1] PULL | KNOT[1] PULL | FLEXUAL[2] MODULUS | FLEXUAL[3] FATIGUE | ELONGATION AT BREAK | TENACITY[4] |
|---|---|---|---|---|---|---|
| Example 1 Copolymer | 75,256 | 41,055 | $0.54 \times 10^5$ | 12,972 | 53% | 4.6 |
| Example 2 Copolymer | 80,049 | 38,485 | $1.31 \times 10^5$ | 6,665 | 36% | 4.6 |
| Example 3 Copolymer | 51,600 | 47,348 | $0.99 \times 10^5$ | — | 49% | 4.6 |
| DERMALON ® | 70,200 | 49,400 | $6.45 \times 10^5$ | 519 | 37% | 4.2 |
| SURGILENE ® | 64,000 | 45,000 | $9.98 \times 10^5$ | 807 | 24% | 5.3 |

[1]pounds per square inch, ASTM D2256
[2]pounds per square inch, ASTM D790
[3]Cycles to failure, Folding Endurance Tester, Tinius Olsen Co.
[4]Grms./Denier, ASTM D2256

We claim:

1. A annealed non-absorbable monofilament sterile surgical suture or ligature having an attached needle comprising a polymeric block (A) consisting of a polyalkylene ether of the formula

having a number average molecular weight of from about 500–3000 wherein R is a straight or branched chain alkyl group of from about 2 to 10 carbon atoms and $R_2$ is 1,4-phenylene or cyclohexylene and n is the number of repeating units; and a polymeric block (B) which is the reaction product of an aromatic dicarboxylic acid or a cycloaliphatic acid, and a short chain aliphatic or cycloaliphatic diol, having the formula

wherein $R_1$ is a straight or branched chain alkyl group of from about 2 to 10 carbon atoms or a cyclic group having the formula

and $R_2$ is 1,4-phenylene or cyclohexylene, said block (B) comprising from about 30% to 95% of said copolymer, and said copolymer having a number average molecular weight of from about 25,000 to 30,000, such that said suture has good flexibility, good fatigue life and high tensile strength.

2. The surgical suture or ligature of claim 1, wherein the polymeric block (B) comprises from about 50% to 85% of the copolymer.

3. The surgical suture or ligature of claim 1, wherein the polymeric block (B) comprises from about 55% to 80% of the copolymer.

4. The surgical suture or ligature of claim 1, wherein R is selected from the group consisting of ethylene, propylene or butylene.

5. The surgical suture or ligature of claim 4, wherein R is butylene.

6. A surgical suture package comprising a sterile enclosure and therein a non-absorbable monofilament sterile surgical suture or ligature of claim 1.

7. The surgical suture package of claim 6 wherein R is butylene.

8. The surgical suture or ligature of claim 1 or 3 or 5 or 7 wherein said suture or ligature is heated at constant length.

* * * * *